United States Patent [19]
Burrow et al.

[11] Patent Number: 5,214,821
[45] Date of Patent: Jun. 1, 1993

[54] LOW CONTAMINATION SWAB EMPLOYING TUBULAR KNIT FABRIC

[75] Inventors: Simon W. Burrow, Pasadena; David P. Nobile, Rancho Cucamonga, both of Calif.

[73] Assignee: The Morgan Crucible Company plc, Windsor, England

[21] Appl. No.: 697,308

[22] Filed: May 7, 1991

[51] Int. Cl.$^5$ ............................................. A47L 13/10
[52] U.S. Cl. ................................... 15/210.1; 15/209.1; 15/225; 604/1
[58] Field of Search ............. 15/209.1, 210.1, 211, 15/223, 225, 226, 228, 244.1; 300/21; 604/1

[56] References Cited

U.S. PATENT DOCUMENTS

| | | |
|---|---|---|
| 101,997 | 4/1870 | Greve . |
| D. 249,364 | 9/1978 | Julius . |
| 982,232 | 1/1911 | Bartholomew . |
| 1,256,831 | 2/1918 | Rogers . |
| 1,388,960 | 8/1921 | Lerch . |
| 1,563,866 | 12/1925 | Kortejarvi . |
| 1,629,436 | 5/1927 | Capri . |
| 1,682,657 | 8/1928 | Blank . |
| 1,766,192 | 6/1930 | Schlegel . |
| 1,866,862 | 7/1932 | Prestwich et al. .............. 15/211 |
| 2,006,539 | 7/1935 | Deford . |
| 2,254,235 | 9/1941 | Mutch ............................ 15/244.1 |
| 2,510,490 | 6/1950 | Ager ................................... 604/1 |
| 2,737,959 | 3/1956 | Soldan . |
| 2,807,039 | 9/1957 | Butler . |
| 3,203,418 | 8/1965 | Johnston ........................... 604/1 |
| 3,542,025 | 11/1970 | Gustafson . |
| 3,591,885 | 7/1971 | Fritzen, Jr. ...................... 15/210.1 |
| 3,618,609 | 11/1971 | Glick et al. . |
| 3,626,946 | 12/1971 | Messey . |
| 3,724,018 | 4/1973 | Sills ................................. 15/244.1 |
| 3,724,463 | 4/1973 | Vail . |
| 4,175,560 | 11/1979 | Knoll . |
| 4,259,955 | 4/1981 | Ritter ............................. 15/210.1 |
| 4,627,127 | 12/1986 | Dupre . |
| 4,888,229 | 12/1989 | Paley et al. . |

Primary Examiner—Harvey C. Hornsby
Assistant Examiner—Mark Spisich
Attorney, Agent, or Firm—Kilpatrick & Cody

[57] ABSTRACT

A swab having an absorbent end comprising a material strip of tubular knit fabric wrapped with a first blind end, helically to a tip and reverse helically to a termination point distal from the tip provides low contamination for use in clean room processes. Lost fibers or lint are precluded by the trapped fiber edges of the material strip forming the absorbent tip of the swab while burying of the first end of the material strip in the blind wrap and combined sealing, severing, and adhering of the second end of the material strip to complete the swab distal from the tip, further precludes fiber contamination.

6 Claims, 4 Drawing Sheets

LOW CONTAMINATION SWAB EMPLOYING TUBULAR KNIT FABRIC

FIELD OF THE INVENTION

The present invention relates to low contamination swabs for clean room applications for electronics, integrated circuits or other contamination sensitive manufacturing operations. In particular, the invention provides a swab which essentially eliminates lost fibers or lint from the swab through the use of a tubular knit fabric having sealed ends to comprise the absorbing material of the swab and employing an over wrap technique burying a first sealed end within the swab and terminating the wrap with a second sealed end spaced from the tip of the swab.

BACKGROUND OF THE INVENTION

Electronic components, integrated circuits, and many other modern articles of manufacture require extreme cleanliness in the processes used in their fabrication. For many such articles the application or removal of solvents, process debris, and other contaminants must be accomplished using swabs, wipes, or similar means. These swabs or wipes must in turn, be very clean and must avoid the addition of any further particulate or residual contaminants to the process or product. Most swabs presently used in such processes are made from woven or foam materials. Various means for preventing the loss of fibers or lint from the swab have been employed to preclude contamination of the article being cleaned. The use of nonwoven or foam materials for swabs has been employed to partially remedy fiber contamination problems, however, linting, flaking, or other degradation of these materials produce similar contamination difficulties.

The size and cleaning application needed for various articles of manufacture additionally requires a range of swab sizes and cushioning of the swab tip. For example, extremely fine cleaning work may require a swab having a narrow or rimmed tip for access to the part to be cleaned. For various operations requiring scrubbing, a relatively stiff or uncushioned tip may be desirable while for other applications a highly cushioned tip in either a radial direction, with respect to the swab stick, or a longitudinal direction may be desirable.

The material employed for the tip of a swab must allow cleaning of the material itself to avoid other contamination of the manufacture from the swab. For example, current swabs employing bleached cotton may introduce chlorides as contaminates in the manufacturing process. The chemical composition of the material used in the swab and the likelihood of retaining contaminates from the process used in cleaning the material contribute to the quality of the swab produced.

SUMMARY OF THE INVENTION

The swab of the present invention includes an elongated handle for manipulation by the user with an absorbing tip mounted at one or both ends of the handle. The absorbing tip comprises an absorbing material strip which is wrapped about the handle. The material strip is knitted fabric with trapped fiber edges. A first end of the material strip is adjacent a surface of the handle and over wrapped by the material strip to provide a blind wrap to capture any loose fibers in the end of the material strip. The material strip is helically wound over an end of the handle to form a tip and wound in a reverse helix from the tip to a termination point on the handle. A second end of the material strip is affixed to the handle at the termination point. The termination point is spaced from the tip of the swab thereby, avoiding contamination by any loose fibers from the second end of the material strip.

A preferred embodiment of the present invention employs a monofilament polyester fabric for the material strip which is configured in a tubular knit. Compressing of the tubular knit into a flat strip provides the desired trapped fiber edges for the swab. Use of a monofilament polyester allows heat sealing of the ends of the material strip to further preclude any fiber loss thereby further reducing contamination from the swab.

Manufacturing of the swab is accomplished by placing the first end of the material strip adjacent the handle and wrapping the material strip over the first end, continuing the wrapping helically past the end of the handle to the tip followed by wrapping the material strip in a reverse helix from the tip to the termination point. The material strip is then severed making the second end on the material strip which is adhered to the handle. The monofilament polyester fabric allows the use of a hot knife or iron for severing the material strip. The iron may be employed to simultaneously sever the material strip, seal the second end, and adhere the material strip to the handle. Proper adjustment of temperature and sizing of the hot knife is employed to simultaneously accomplish sealing of the material strip on the severed portion to provide a sealed first end for wrapping a subsequent swab.

DESCRIPTION OF THE DRAWINGS

The foregoing and other advantageous and distinguishing features of the invention are described in detail subsequently in reference to the following drawings and are recited in the appended claims.

DETAILED DESCRIPTION OF THE INVENTION

Figure 1:
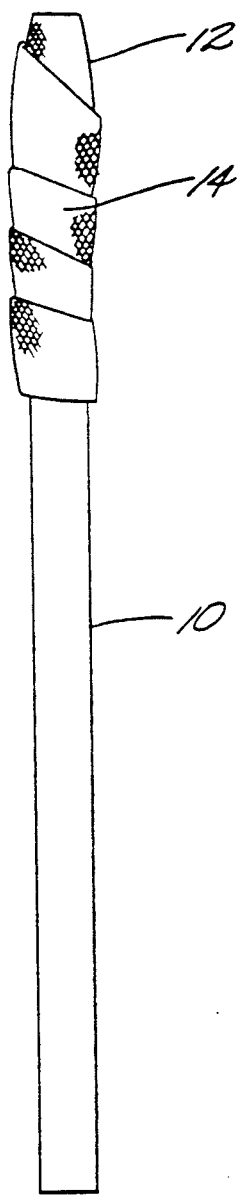
FIG. 1 is a side view of the completed swab.

Referring to the drawings, FIG. 1 shows the configuration of a completed swab. An elongated handle 10 is provided for manipulation of the swab by the user. An absorbent tip 12 for the swab is created by winding a material strip 14 around the end of the handle as will be described in greater detail subsequently. An absorbing tip may be placed at one or both ends of the handle as desired during fabrication. Predominate use of the swab is in clean room applications for manufacturing operations in electronics integrated circuits. Such uses typically incorporate procedures precluding reuse of swabs thereby resulting in preference for "single ended" swabs.

The material strip employed for the absorbent tip of the swab has trapped fiber edges to preclude contamination of the work piece or the process in which the swab is employed by eliminating the presence of loose fibers at the edge of the fabric. In the preferred embodiment a tubular knit fabric is employed for the material strip. The tubular knit fabric provides a continuous cross section which when flattened to form a strip or ribbon, provides edges in which all fibers are trapped as a portion of the knit. The tubular structure avoids any termination of the warp or weave at the edge of the material strip.

Figure 2:
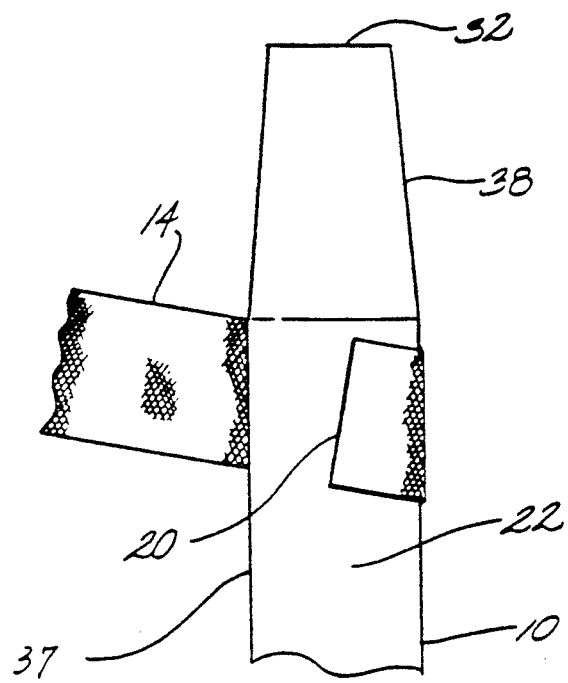
FIG. 2 is a partial side view of the swab employing a handle with a tapered end demonstrating the initiation of wrapping the material strip.

The material strip is wound on the handle of the swab in a helical wrap initiated as shown in FIG. 2. A first end 20 of the material strip is placed adjacent the surface 22 of the handle. In the preferred embodiment, the handle is a substantially cylindrical molding of glass filled nylon or similar material. Those skilled in the art will recognize that hexagonal or rectangular cross sections as well as various materials may be employed for the handle. The material strip is wrapped around the handle to overlap the first end thereby creating a blind wrap which avoids exposure of the first end to the exterior of the absorbent tip of the swab.

Figure 3:
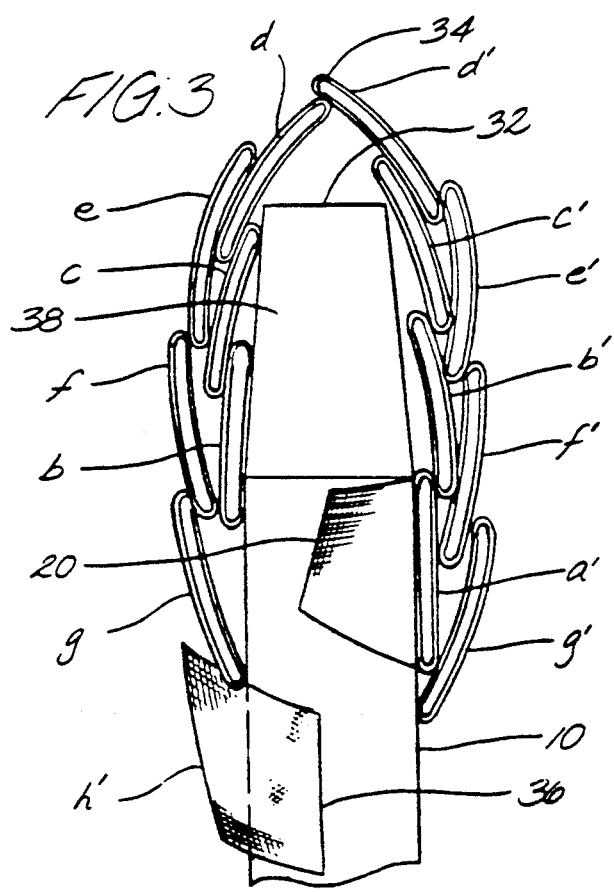
FIG. 3 is a partial cutaway side view of the swab demonstrating the overlaying of the material strip in the helical winding to the tip and reverse helical winding from the tip to the termination point on a handle employing a tapered end. The wrap demonstrating a closed tip of medium bulk.

As best seen in FIG. 3, the material strip is wrapped helically toward the end 32 of the handle. The layers of the tubular knit fabric are shown in cross section in FIG. 3. Each wrap is designated by the lower case letters a–h with the retreating wrap designated as "'". For example, a' is the retreating cross section of the first layer of the wrap, b is the advancing section of the second wrap, and b' is the retreating section of the second wrap.

The helical wrapping of the material strip extends past the end of the handle to form a tip 34. The material strip is then wound in a reverse helix down the handle from the tip. The reverse helical wrap concludes at the second end 36 of the material strip at a termination point distal from the tip of the swab. Spacing of the second end from the tip reduces likelihood of contamination by loose fibers from the second end at the tip of the swab which typically has the greatest functional use in cleaning or other uses for which the swab is employed. The termination point may be on a bare surface of the handle or on the underlying helical wrap as will be described in greater detail subsequently.

The configuration of the tip of the swab may be varied through the overlap of wraps on the material strip and the number of wraps extending beyond the end of the handle. The cross section shown in FIG. 3 obtains a medium bulk through average overlap distance on the individual wraps of the material strip. A pointed tip is achieved by extending the wrap beyond the end of the handle.

Figure 4:
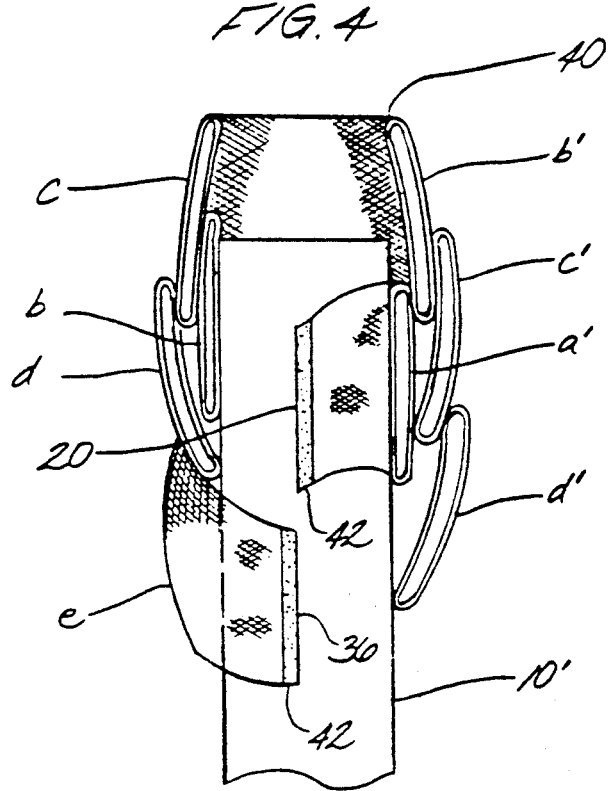
FIG. 4 is a side partial cutaway of the swab employing a handle with an untapered end demonstrating an open tip wrap of low bulk.

FIGS. 2 and 3 further demonstrate the use of a handle having a main body portion 37 and a tapered portion 38 extending from the end of the handle having a lesser diameter at the end and tapering to the primary diameter of the handle in the main body portion. Tapering of the handle also assists in shaping of the tip of the swab. FIG. 4 demonstrates an alternative wrapping of the material strip on an untapered handle 10'. The configuration shown in FIG. 4 provides low bulk using minimal overlap in the wrapping of the material strip and a tip with an open rim 40.

The material strip shown in FIG. 4 also demonstrates sealing of the first and second ends in the preferred embodiment. A monofilament polyester fabric is employed for the tubular knit material. Application of sufficient heat to this material through the use of a hot knife or other process fuses the fibers in the end of the material thereby providing a sealed edge 42. One or both ends of the material strip may be sealed as shown in FIG. 4.

Figure 5:
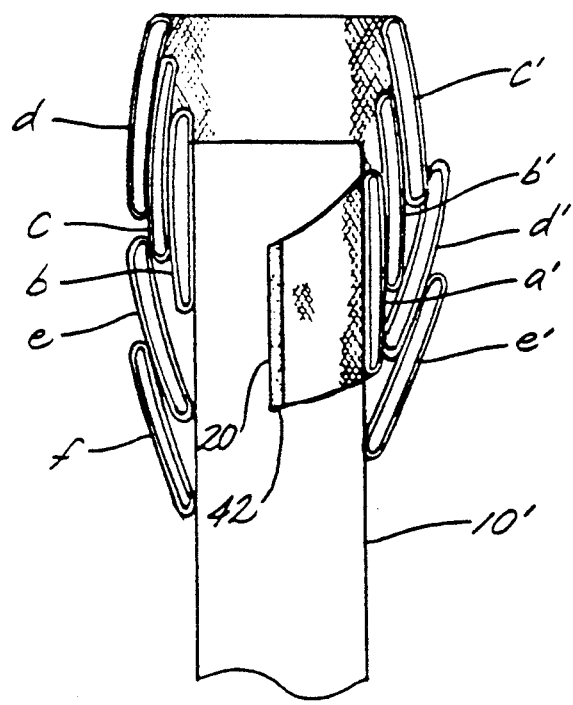
FIG. 5 is a side partial cutaway view of the swab employing an untapered handle with an open tip wrap with higher bulk than shown in FIG. 4.

FIG. 5 demonstrates a high bulk configuration for the swab obtained by employing high overlap on the various wraps of the material strip. A greater number of layers achieved by greater overlap in the wrap provides greater bulk near the tip of the swab for greater absorbency or cushioning during use of the swab.

Figure 6:
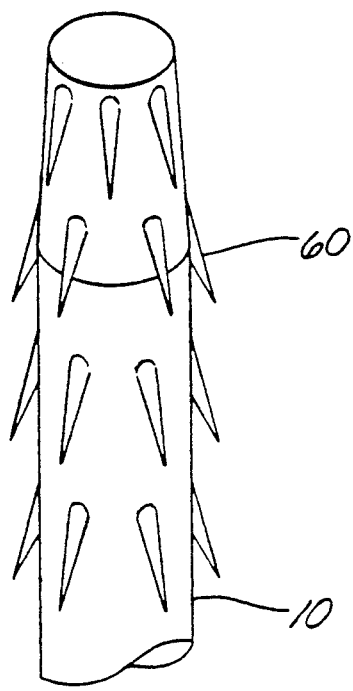
FIG. 6 is a partial side view of the swab handle employing a tapered end with restraining barbs.

Referring now to FIG. 6 an alternative configuration of the handle is shown, which incorporates barbs to arrest the fabric of the material strip. The embodiment shown in FIGS. 2–5 employs friction between the first end of the material strip and the surface of the handle created by tensioning of the overlying wraps of the material strip. Alternatively, an adhesive may be employed to fix the first end of the material strip to the handle. In some applications avoiding the use of an adhesive may preferred to prevent possible contamination of the swab and work piece. Employing a handle as shown in FIG. 6 allows the fabric of the first end on the material strip to be engaged by barbs on the handle thereby avoiding reliance on friction to maintain the position of the first end of the material strip. Additionally, portions of the material strip contact the handle in the helical or reverse helical wrapping of the material strip which may be arrested by the barbs on the handle.

Figure 7:
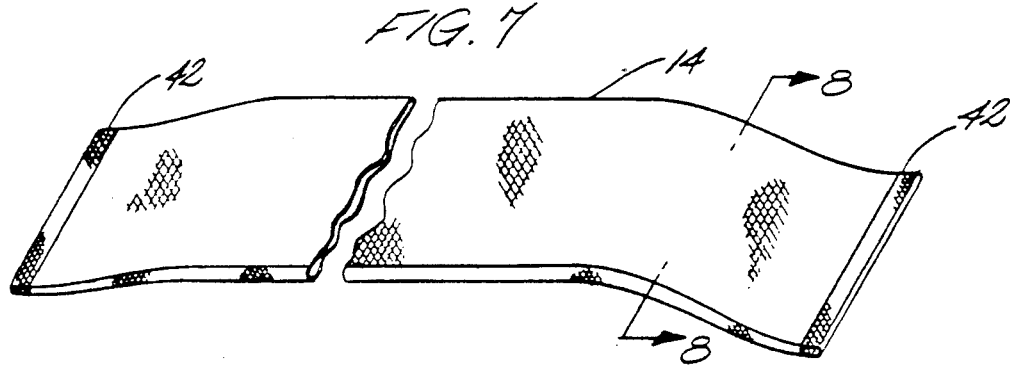
FIG. 7 is a pictorial representation of the tubular knit material strip having sealed ends.

Referring now to FIG. 7, the preferred embodiment for the material strip having trapped fiber edges is shown. A tubular knit fabric is employed for the material strip.

Figure 8:
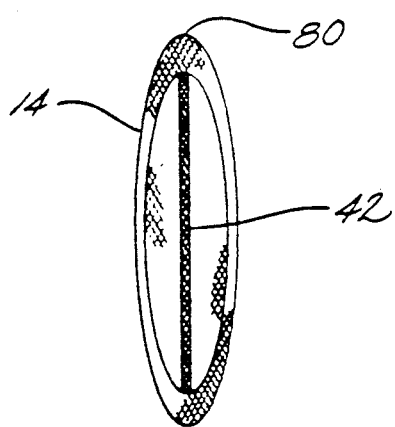
FIG. 8 is an end view of the material strip along line 8—8 in FIG. 7 demonstrating the tubular knit fabric with a sealed end.

As best seen in FIG. 8 the tubular knit fabric flattens to provide the material strip with trapped fiber edges 80. In the embodiment shown in the drawings a plain jersey knit is employed on a tubular knitting machine to provide the material strip. In a preferred embodiment a monofilament polyester, nylon or polypropelene at a density of approximately 70 denier is employed. Other densities and materials may be employed to produce desired swab characteristics for absorbancy, bulk, and roughness.

Use of a monofilament polyester allows heat sealing of the ends of the material strip as previously described and shown in FIG. 7. Use of a hot knife, wire, iron or other tool for severing the tubular knit fabric allows simultaneous severing and sealing of the end of the material strip. The sealed end obtained in this process causes the individual monofilaments to flow and adhere to one another avoiding loose fibers in the ends of the material strip to reduce contamination from the swab. In the preferred embodiment polyester plain jersey tubular knit fabric produced by Adele Knits, Inc., 800 Chatham Road, Winston-Salem, N.C. 27101 is used.

The manufacturing process for the swabs comprises a blind end helical wrapping of the material strip on the handle. As previously described with respect to FIG. 2, the wrap is initiated by placing a first end of the material strip on the surface of the handle and over wrapping the material strip to secure the first end. The use of adhesive or barbed protrusions on the handle to affix the first end to the handle provide options dependent on processing requirements and sensitivity to various contamination sources. The blind wrap created by over wrapping the first end, eliminates a major source of fiber contamination in the swab. Sealing of the ends as previously described further limits this contamination source. Helical wrapping of the material strip past the end of the handle to the swab tip is accomplished with varying tension and overlap of the material strip to achieve desired bulk in the swab tip and to obtain the desired tip configuration. As previously described, a tapered end on the handle provides additional control for tip size and bulk.

A reverse helical wrap of the material strip from the tip to the termination point completes the swab, with tension and overlap on the material strip again contributing to the bulk produced in the tip. The second end of the material strip is affixed to the handle or to the layers of the initial helical wrap of the material strip at the termination point of the wrap to preclude unwrapping of the material strip from the handle. Compatibility of materials between the handle and the material strip for the preferred embodiment (nylon handle and polyester material strip) allows sealing, severing, and adhering of the second end of the material strip in a single step employing a hot knife or hot iron as previously described. However, compatibility is not necessary if the termination point overlies the helical wrap. Material tension at the second end is maintained during adhering of the second and to ensure frictional engagement of the helical and reverse helical wrap layers. Heating of the material strip to approximately 600° F., seals the second end to preclude fiber loss, severs the material strip and adheres the material strip to the nylon handle by creating material flow between the material strip and handle. Operation of the hot iron to seal and sever the second end of the material strip simultaneously seals the material strip providing a first end for use in fabrication of a subsequent swab.

Having now described the invention in detail, as required by the patent statues, those skilled in the art will recognize modifications and alterations to the invention to accommodate specific needs. Such alterations and modifications are within the scope and spirit of the invention as defined in the following claims.

What is claimed is:

1. A low contamination swab comprising:
a handle having a substantially cylindrical surface, and a tubular knit material strip having a first sealed end adjacent a portion of the surface of the handle spaced from an end thereof, the material strip overwrapping the first end to frictionally engage the first end with the surface, the material strip further being wrapped helically to extend beyond the end of the handle to a tip and wrapped in a reverse helix to a termination point distal the end of the handle, a second end of the material strip adhered to the handle at the termination point.

2. A low contamination swab comprising:
an elongated handle, and an absorbing material strip comprising a tubular knit fabric having first and second opposite ends, the first end adjacent a surface of the handle spaced from an end thereof and overwrapped by the material strip, the material strip being further helically wound to a tip extending from the end of the handle, and wound in a reverse helix from the tip to a termination point distal the end of the handle, the second end affixed to the handle at the termination point.

3. A swab as defined in claim 2 wherein the tubular knit fabric is monofilament polyester.

4. A swab as defined in claim 3 wherein the tubular knit fabric is a plain Jersey knit.

5. A swab as defined in claim 2 wherein the handle has a main body having a primary diameter and includes a tapered portion extending from the end of the handle to the main body, the tapered portion having a lesser diameter at the end of the handle and tapering to the primary diameter at the main body.

6. A swab as defined in claim 2 wherein the helical and reverse helical wrap places portions of the material strip in contact with the handle, and the handle includes barbs to arrest the first end and the portions of the material strip in contact with the handle.

* * * * *